(12) United States Patent
Blanchon et al.

(10) Patent No.: US 9,018,590 B2
(45) Date of Patent: Apr. 28, 2015

(54) DEVICE FOR ADDRESSING LINES OF A CONTROL CIRCUIT FOR AN ACTIVE DETECTION MATRIX

(75) Inventors: David Blanchon, Moirans (FR); Benoît Racine, Moirans (FR)

(73) Assignee: Trixell S.A.S., Moirans (FR)

( * ) Notice: Subject to any disclaimer, the term of this patent is extended or adjusted under 35 U.S.C. 154(b) by 154 days.

(21) Appl. No.: 14/117,010

(22) PCT Filed: May 9, 2012

(86) PCT No.: PCT/EP2012/058555
§ 371 (c)(1),
(2), (4) Date: Dec. 13, 2013

(87) PCT Pub. No.: WO2012/152836
PCT Pub. Date: Nov. 15, 2012

(65) Prior Publication Data
US 2014/0321618 A1    Oct. 30, 2014

(30) Foreign Application Priority Data

May 10, 2011    (FR) ...................................... 11 54029

(51) Int. Cl.
*G01T 1/24*    (2006.01)
*G01T 1/172*    (2006.01)
*H04N 5/345*    (2011.01)
*H04N 5/376*    (2011.01)
*G01N 23/04*    (2006.01)

(52) U.S. Cl.
CPC .............. *G01T 1/172* (2013.01); *H04N 5/3452* (2013.01); *H04N 5/376* (2013.01); *G01N 23/04* (2013.01)

(58) Field of Classification Search
CPC .......... G01T 1/2928; G01T 1/24; G01T 1/247
USPC .................................................... 250/370.09
See application file for complete search history.

(56) References Cited

U.S. PATENT DOCUMENTS

| 5,536,932 A | 7/1996 | Hack et al. |
| 6,064,713 A | 5/2000 | Lebrun et al. |
| 6,163,029 A * | 12/2000 | Yamada et al. .......... 250/370.09 |
| 7,728,889 B2 | 6/2010 | Apard et al. |
| 2002/0172327 A1 | 11/2002 | De Groot |

(Continued)

FOREIGN PATENT DOCUMENTS

| FR | 2743662 A1 | 7/1997 |
| FR | 2861242 A1 | 4/2005 |

(Continued)

*Primary Examiner* — Marcus Taningco
(74) *Attorney, Agent, or Firm* — Baker Hostetler LLP

(57) ABSTRACT

A device is provided for addressing the rows of an active detection matrix for imaging by ionizing radiations comprising a plurality N of rows n of pixels, the addressing device being produced on a substrate on which the matrix is also producing and mainly comprising thin film transistors of single N or P type. The row addressing device can comprise a plurality of stages suitable for delivering at their respective outputs switching signals for switching the high and low levels of a signal applied to switching devices at the output on a corresponding row of the matrix and being characterized in that each stage comprises an input stage and an output stage, the input stage delivering an activation signal for the output stage, the output stage delivering, in case of activation, said switching signal for the corresponding row n.

16 Claims, 5 Drawing Sheets

(56) References Cited

U.S. PATENT DOCUMENTS

2004/0114719 A1\* 6/2004 Endo .................... 378/98.8
2006/0065944 A1\* 3/2006 Mochizuki et al. ........... 257/444
2008/0244228 A1\* 10/2008 Overdick et al. ............. 712/39
2011/0102623 A1 5/2011 Ebihara

FOREIGN PATENT DOCUMENTS

| GB | 2317742 A | 4/1998 |
| WO | 2011027661 A1 | 3/2011 |

\* cited by examiner

DEVICE FOR ADDRESSING LINES OF A CONTROL CIRCUIT FOR AN ACTIVE DETECTION MATRIX

CROSS-REFERENCE TO RELATED APPLICATIONS

This application is a National Stage of International patent application PCT/EP2012/058555, filed on May 9, 2012, which claims priority to foreign French patent application No. FR 1154029, filed on May 10, 2011, the disclosures of which are incorporated by reference in their entirety.

FIELD OF THE INVENTION

The present invention relates to a row addressing device of a control circuit suitable for controlling the rows of an active detection matrix. It applies notably to active matrices used, for example, for detection purposes in ionizing radiation imaging devices, for example using x rays, such as TFT (Thin Film Transistor)-type plates.

BACKGROUND

An active detection matrix, for example, a TFT-type plate that makes it possible to acquire an image representative of an incident radiation on a detector assembly, comprises a plurality of electro-optical cells arranged in rows and columns. In an ionizing radiation imaging application, a detector assembly can comprise such a detection matrix, then making it possible to acquire an image representative of the incident radiation on the detector assembly. Each cell of the arrangement can be controlled by a switching device, and can, for example, be controlled by the application of an electrical field applied via two electrodes bracketing the cell. The assembly consisting of the switching device, the electrodes and the cell is commonly designated "pixel". The switching device can, for example, be formed by a switching transistor. For example, each row of the matrix can be connected to the gates of the switching transistors of a row of pixels. Thus, for each frame, the rows can be selected in sequence, one after the other in a direction of scanning of the rows of the matrix, during a row selection time corresponding to a fraction of the duration of the frame, allowing for the application of appropriate signals to the pixels of the row, for example voltages on the electrodes. Thus, the selection of a row corresponds to the application, during a corresponding row selection time, of a high-level signal controlling the passing state of the switching devices of the corresponding row of pixels. Outside of the row selection time, the switching devices are maintained in a blocked state via the application of an appropriate low-level signal. For example, when the switching devices are transistors, the signals to be applied then being voltages, it is usual practice to use VGon to designate the voltage corresponding to the high level and therefore to the passing state of the switching transistor, and VGoff to designate the voltage corresponding to the low level and the blocked state of the switching transistor.

In a manner known per se from the prior art, the rows can be controlled by control circuits comprising one or more shift registers in series, each of the shift registers comprising a plurality of cascaded stages, each stage being suitable for switching the high and low levels of the signal applied to the switching devices at the output on a corresponding row of the matrix, according to the sequencing of the selection of the rows, for example according to a vertical scanning. The control circuits can be implemented in integrated circuits, one and the same integrated circuit being able, for example, to comprise a plurality of control circuits for a plurality of rows of the matrix. The integrated circuits can, for example, be external to the matrix, and be connected thereto by wired means, for example by flexible ribbon cables. The integrated circuits can, for example, be directly mounted on the flexible ribbon cables, the latter connecting them not only to the matrix but also to a control and power supply circuit. Such systems however present the drawback of requiring complex production methods, and involve a large number of checks during fabrication. As well as a large number of repairs, due to the number of potential defects linked to all the steps of the production methods. An example of an existing system comprising integrated control circuits arranged on flexible ribbon cables is described in detail hereinbelow with reference to FIG. 1.

Another drawback with the known addressing systems is that the latter require the rows to be addressed one after the other, without it being permitted for a row not to be addressed; thus, the rows are addressed one after the other, and there is no pause between the addressing of two successive rows, the latter point potentially being particularly prejudicial when the matrix is used for detection purposes, for which it is necessary to allow an integration time for the charges originating from the pixels of the plate. Furthermore, these systems require all of the matrix to be addressed, according to a fixed addressing mechanism; now, it may in practice prove pointless, even prejudicial, to address all of the plate, for example in typical uses where the plate is used for detection purposes, notably in the context of x-ray imaging applications, in which the operator or the practitioner frequently takes care to view with an enhanced accuracy specific parts of the imaged scene, via so-called "zoom" operations.

The U.S. Pat. No. 5,536,932 describes a polysilicon multiplexer for two-dimensional image detection matrices.

The patent application published under the reference GB 2,317,742 describes an imaging device.

The patent application US 2002/172327 describes a radiological image detection system for a scanning x-ray generator.

SUMMARY OF THE INVENTION

One aim of the present invention is to mitigate at least the abovementioned drawbacks, by proposing a control circuit for an active detection matrix for ionizing radiation imaging, such as a TFT plate, having a compact and robust structure, essentially comprising TFT transistors of single N or P type.

According to a specific feature of the present invention, it is permitted to address the rows of the matrix in two stages, thus offering a time window between the addressing of two successive rows.

One advantage of the invention is that the addressing device according to one of the embodiments of the invention described hereinbelow offers the possibility of not addressing certain rows, thus increasing the overall speed and efficiency of the system.

Another advantage of the invention is that the row addressing device according to one of the embodiments of the invention offers the possibility of proceeding with an advantageous reset of the rows.

To this end, the subject of the invention is a device for addressing the rows of a detection matrix for imaging by ionizing radiations, the detection matrix comprising a plurality N of rows n of pixels and being produced on a substrate, the addressing device being characterized in that it is also produced on said substrate mainly from thin-film transistors of single N or P type, the addressing device comprising a plurality of stages suitable for delivering, at their respective outputs, switching signals for switching between the high and low levels of a signal applied to switching devices on a corresponding row of the detection matrix, and comprising a plurality of stages suitable for delivering, at their respective outputs, switching signals for switching between the high and low levels of a signal applied to switching devices at the output on a corresponding row of the matrix and being characterized in that each stage comprises an input stage and an output stage, the input stage delivering an activation signal for the output stage, the output stage delivering, in case of activation, said switching signal for the corresponding row n.

In one embodiment of the invention, each input stage of a row n comprises an output restoring the activation signal, an output transistor of the input stage, transmitting a pulse of a clock signal at the activation output, its gate being connected to an internal node of the input stage, its source being linked to the activation output row and its drain receiving the signal of a first clock, a first control transistor of the input stage being suitable for precharging the gate of the output transistor of the input stage, its source being connected to the gate of the output transistor of the input stage, its gate and its drain being linked to the activation output of the stage of the preceding row, a second control transistor of the input stage being suitable for discharging the gate of the output transistor of the input stage, its drain being connected to the gate of the output transistor of the input stage.

In one embodiment of the invention, each output stage of a row n can comprise an output restoring the switching signal of the row n, an output transistor of the output stage, transmitting a pulse of a clock signal at the output, of which the gate is connected to an internal node of the output stage, the source is linked to the output of the output stage and the drain receives the signal of a third clock, a first control transistor of the output stage being suitable for precharging the gate of the output transistor of the output stage, its source being connected to the gate of the output transistor of the output stage, its gate and its drain being linked to the activation output of the input stage, a second control transistor of the output stage being suitable for discharging the gate of the output transistor of the output stage, its drain being connected to the gate of the output transistor of the output stage.

In one embodiment of the invention, a compensation capacitor of the input stage can be arranged between the signal of a second clock, in phase opposition to the signal of said first clock.

In one embodiment of the invention, a step-up capacitor of the input stage can be connected between the gate and the source of the output transistor of the input stage.

In one embodiment of the invention, a discharge transistor of the input stage can be connected to the activation output at the output of the input stage, its gate being linked to the gate of the second control transistor of the input stage and to the activation output signal of the next stage n+1.

In one embodiment of the invention, a compensation capacitor of the output stage can be arranged between the signal of a fourth clock, in phase opposition to the signal of said third clock.

In one embodiment of the invention, a step-up capacitor of the output stage can be connected between the gate and the source of the output transistor of the output stage.

In one embodiment of the invention, a discharge transistor of the output stage can be connected to the output of the output stage, its gate being linked to the gate of the second control transistor of the output stage and to the activation output signal of the next stage.

In one embodiment of the invention, each input and output stage of a row n can comprise a reset switch configured to set all the transistors in their blocked state.

In one embodiment of the invention, the reset switches can be formed by reset transistors, a reset transistor of the input stage having a gate controlled by a pulse of a reset signal, its source being connected to the sources of the second control transistor of the input stage, and its drain being connected to the drain of the second control transistor of the input stage.

In one embodiment of the invention, the reset switches are formed by reset transistors, a reset transistor of the output stage having a gate controlled by a pulse of a reset signal, its source being connected to the sources of the second control transistor of the output stage, and its drain being connected to the drain of the second control transistor of the output stage.

In one embodiment of the invention, each output stage of a row n can comprise a row reset switch configured to impose a low level on the switching signals.

In one embodiment of the invention, the row reset switch can be formed by a row reset transistor controlled via its gate by a row reset signal, its drain being connected to the source of the output transistor of the output stage, its source being connected to the sources of the second control transistor of the input stage, of the discharge transistor of the input stage, of the second control transistor of the output stage and of the discharge transistor of the output stage.

In one embodiment of the invention, each output stage of a row n can comprise a matrix reset switch configured to impose a high or low level on the detection matrix.

In one embodiment of the invention, the matrix reset switch can be formed by a matrix reset transistor controlled via its gate and its drain by a matrix reset signal, its source being connected to the source of the output transistor of the output stage.

Another subject of the present invention is an integrated circuit comprising a matrix of pixels arranged in a plurality n of rows, the rows being addressed by a plurality n of output stages of a row addressing device according to any one of the embodiments described, also produced in the integrated circuit.

BRIEF DESCRIPTION OF THE DRAWINGS

Other features and advantages of the invention will become apparent on reading the description, given as an example, and in light of the appended drawings which represent.

DETAILED DESCRIPTION

Figure 1:
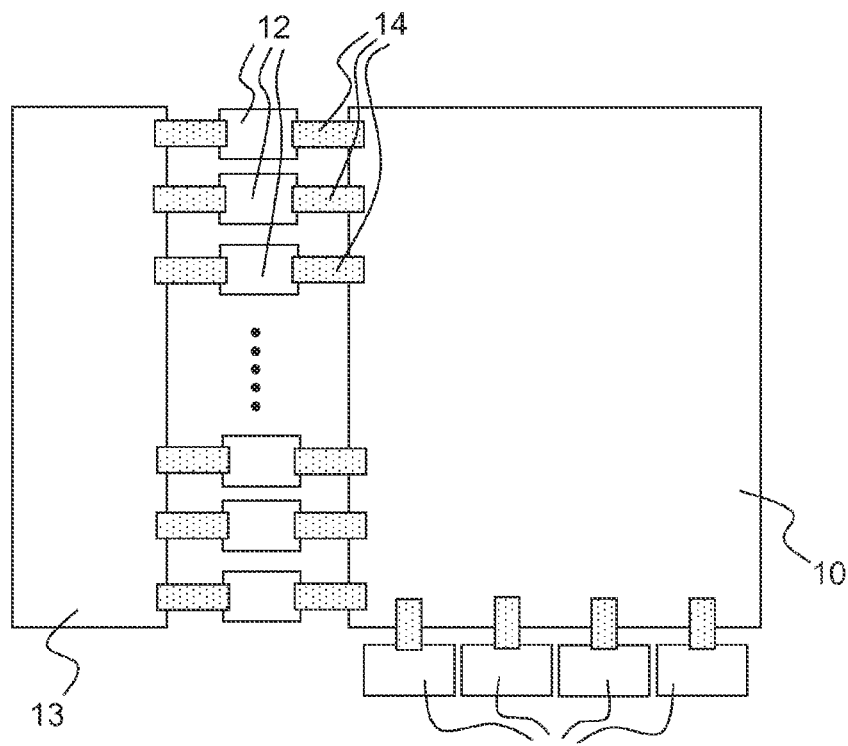
FIG. 1, a diagram illustrating the overall structure of an existing system comprising an active display matrix and associated control circuits, according to a known embodiment.

FIG. 1 shows a diagram illustrating the overall structure of an existing system comprising an active display matrix and associated control circuits, according to an embodiment which is in itself known.

According to a technique which is in itself known, a matrix 10 can be linked to a plurality of column control circuits or charge integration circuits or column addressers 11 controlling the columns of the matrix 10, and to a plurality of row addressers 12. The addressers 11, 12 can be linked on the one hand to one or more electronic boards 13 via flexible ribbon cables 14, and on the other hand to the matrix 10, also via flexible ribbon cables 14. One and the same column addresser 11 can control one or a plurality of columns of the matrix 10; similarly, one and the same row control circuit 12 can control one or a plurality of rows. In a known embodiment, the addressers 11, 12 can, for example, be directly mounted on a single flexible ribbon cable linking them on either side respectively to the electronic board 13 and to the matrix 10.

Figure 2:
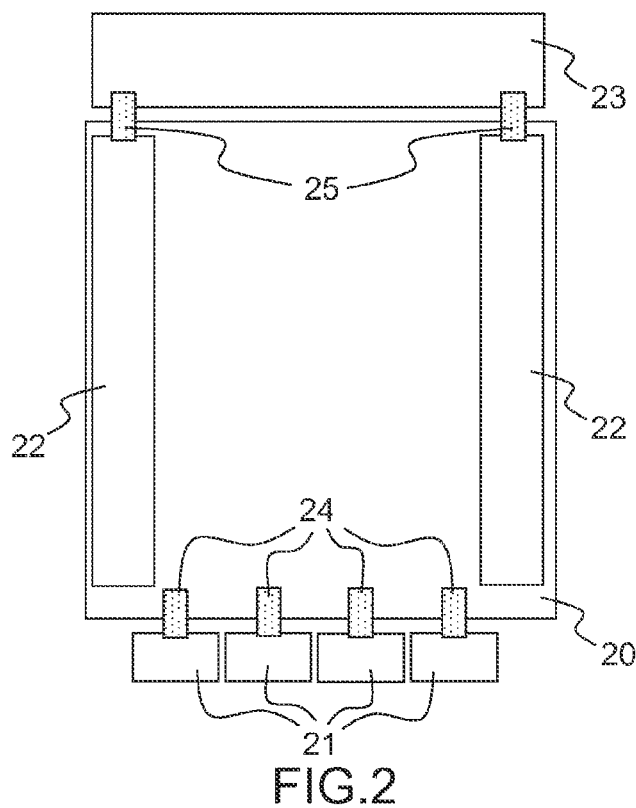
FIG. 2, a diagram illustrating the overall structure of an existing system of integrated structure, comprising an active display matrix and associated control circuits, according to a known embodiment.

FIG. 2 shows a diagram illustrating the overall structure of an existing system of integrated structure, comprising an active display matrix and associated control circuits, according to a known embodiment.

A display matrix 20 can, for example, contain row addressers 22 integrated in its structure. In the example illustrated by FIG. 2, the column addressers 21 can be integrated circuits external to the matrix 20 and connected thereto by flexible ribbon cables 24, in a manner similar to the exemplary embodiment described previously with reference to FIG. 1. The column addressers 21 can also be integrated in the structure of the matrix 20. Flexible ribbon cables 25 can also electrically link the row addressers 22 to an electronic board 23. In the interests of integration, the row addressers 22 can, in an exemplary embodiment, be arranged on either side of the matrix 20.

The present invention proposes to make use of an integrated structure, produced according to a technology that makes it possible to produce semiconductor electronic devices by a deposition of layers on a substrate, for example of amorphous silicon (a-Si), TFT, polycrystalline silicon, organic semiconductor, amorphous gallium indium zinc oxide ($Ga_2O_3$—$In_2O_3$—$ZnO$) type, the semiconductor devices being essentially TFT transistors of single type, that is to say of P type or of N type, the integrated structure forming a device for addressing rows of a detection matrix, used for example in imaging devices, for example x-ray imaging devices. Such an implementation provides a gain in terms of compactness and fabrication cost. It also allows for a gain in terms of efficiency, in practice, if a row is cut or partially cut, the fact of having row addressers on either side makes it possible anyway to address all of the row.

Another advantage obtained by the present invention lies in the fact that the latter makes it possible to address a particular row without requiring a large number of commands for that purpose, whereas the known row addressing devices do not allow for the addressing of a particular row, or else require a number of commands that is not independent of the number of rows used.

Figure 3:
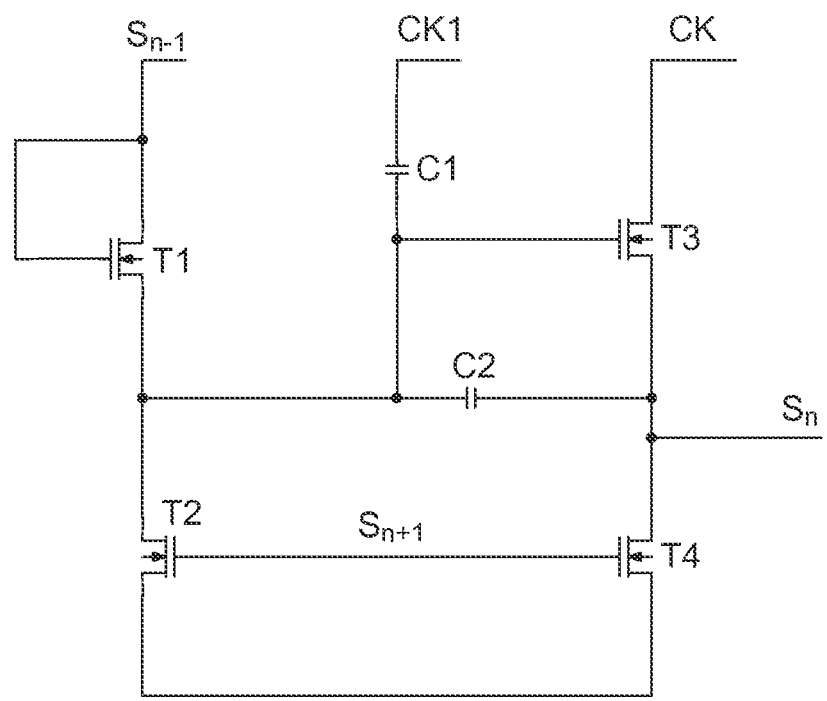
FIG. 3, an electrical circuit diagram illustrating the structure of a register forming a stage of a row addressing device of a display matrix, according to a known embodiment.

FIG. 3 shows an electrical circuit diagram illustrating the structure of a register forming a stage of a row addressing device of a display matrix, according to a known embodiment. Such a structure is, for example, described in the above-mentioned French patent application FR 2,743,662.

A shift register forming a stage n of a row addressing device can comprise an output line restoring an output signal $Sn$; for example, if the matrix comprises N rows, each row n is associated with a stage n, the N stages 1 to N propagating, via their respective outputs S1 to SN, an input pulse formed by a row scanning triggering signal IN transmitting a clock pulse for each new frame. In this way, the rows 1 to N can be selected one after the other. The stage n of the addressing device can comprise an output transistor T3, transmitting a pulse of a clock signal at the output Sn. The output transistor T3 is, for example, a field effect transistor, of the type commonly referred to by the acronym MOSFET. More specifically, the output transistor T3 can be a so-called n type MOSFET transistor, commonly designated by the acronym N-MOS. The gate of the output transistor T3 can be connected to an internal node of the stage of the addressing device, its source can be linked to the output Sn and its drain can receive the signal of a first clock Ck. A step-up capacitor C2 can be connected between the gate and the source of the output transistor T3. A first control transistor T1 is suitable for pre-charging the gate of the output transistor T3. The source of the first control transistor T1 is thus connected to the gate of the output transistor T3. The gate of the first control transistor T1 is controlled by the output Sn−1 of the stage n−1 of the preceding row n−1 addressing device. The gate of the first control transistor T1 of the first stage of the addressing device, corresponding to the first row of the matrix, can be controlled by the row scanning triggering signal IN. The drain of the first control transistor T1 can be linked to an independent voltage, or else to the gate of the first control transistor T1 as in the example illustrated by FIG. 2.

A second control transistor T2 is suitable for discharging the gate of the output transistor T3. The drain of the second control transistor T2 is thus connected to the gate of the output transistor T3. The gate of the second control transistor T2 is linked to the output signal Sn+1 of the stage n+1 of the addressing device, corresponding to the next line n+1. The gate of the control transistor T2 of the stage N of the addressing device, corresponding to the last row N, can be controlled by a specific signal. The source of the second control transistor T2 can, for example, be biased to the voltage VGoff. A compensation capacitor C1 can advantageously be arranged between the signal of a second clock Ck1, in phase opposition to the signal of the first clock Ck. The compensation capacitor C1 makes it possible to compensate the effects of the stray capacitance between the gate and the drain of the output transistor T3 during the switchovers of the signal of the first clock Ck applied to the drain of the output transistor T3.

Advantageously, a discharge transistor T4 can be connected to the output Sn of the stage n of the row addressing device, in order to facilitate the discharge of the output Sn at the end of the row selection phase. The gate of the discharge transistor T4 is linked to the gate of the second control transistor T2.

Figure 4:
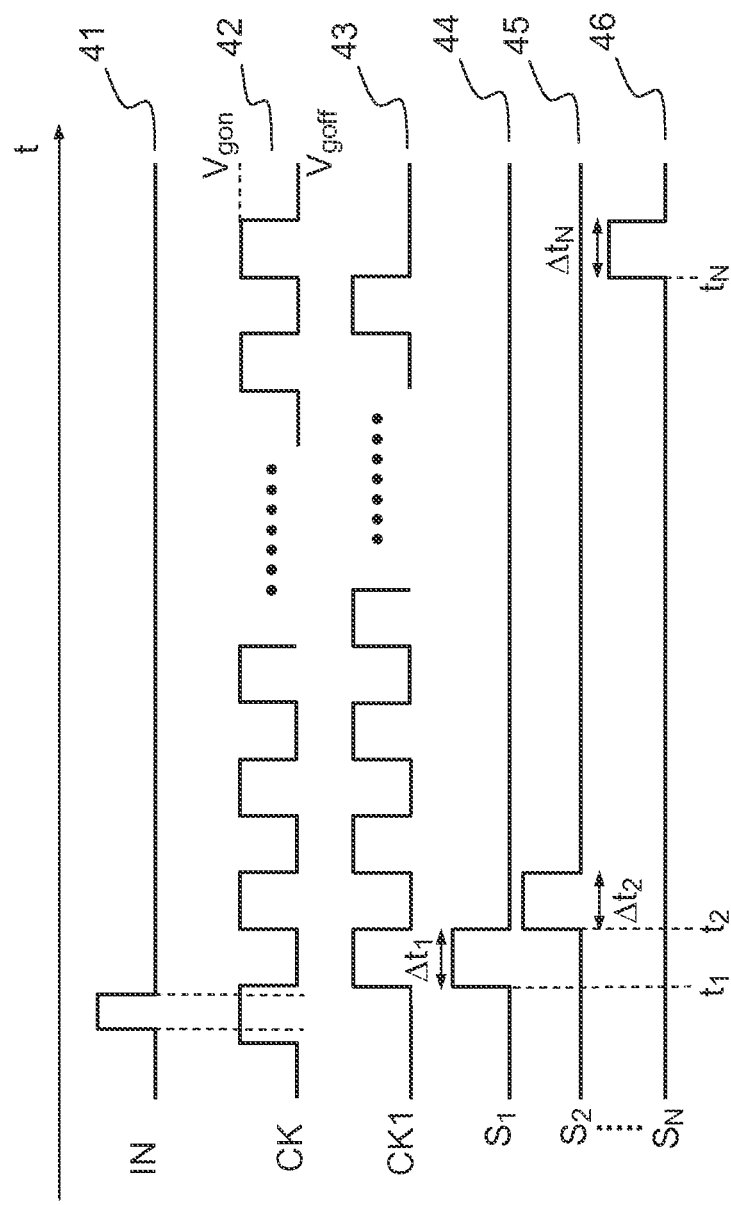
FIG. 4, a timing diagram illustrating the operation of a row addressing device as illustrated by FIG. 3.

FIG. 4 shows a timing diagram illustrating the operation of a row addressing device as illustrated by FIG. 3.

A first timing diagram 41 represents the row scanning triggering signal IN, during a time period corresponding to the transmission of a frame.

A second timing diagram 42 represents, for the same time period, the signal of the first clock Ck; a third timing diagram 43 represents the signal of the second clock Ck1.

A fourth timing diagram 44 represents, for the same time period, the signal of the output S1 of the first stage of the row addressing device; a fifth timing diagram 45 represents the signal of the output S2 of the second stage of the row addressing device; a sixth timing diagram 46 represents the output signal SN of the stage N of the row addressing device.

The logic signals represented by the different timing diagrams 41 to 46 exhibit, for example, a low level corresponding to the level VGoff, and a high level corresponding to the level VGon, these levels making it possible to respectively control the blocked state and the passing state of a transistor.

The scanning of a frame is triggered by the signal IN, transmitting a pulse for each new frame.

This pulse of the signal IN will be "propagated" at the output $S_1$ of the first stage, then from row to row, on the outputs $S_2, S_3, \ldots, S_n, \ldots, S_N$ of the stages 1 to N, such that the rows of the matrix can be selected one after the other, during a corresponding row selection phase, $\Delta t_1, \Delta t_2, \ldots \Delta t_n, \ldots, \Delta t_N$, once per frame, at the rate of the clock signals.

From one stage to the next, the roles of the signals of the clocks Ck and Ck1 are exchanged: for example, in the stages n−1 and n+1, it is the output transistor T3 which receives the signal of the first clock Ck and the compensation capacitor C1 which receives the signal of the second clock Ck1.

The signals of the clocks Ck and Ck1 are complementary. The high level Vgon of the clock pulses is defined so that the switching transistors of the matrix are capable of charging without loss, for example, the video voltage levels to be applied to the electrodes of the pixels, and to allow for the switchover to the passing, and sufficiently conductive, state of the output transistors T3 of the stages of the row addressing device.

The phase of selection $\Delta t_{n-1}$ of the row n−1 begins at an instant $t_{n-1}$ and ends at an instant $t_n$. The phase of selection $\Delta t_n$ of the row n begins at the instant $t_n$ and ends at the instant $t_{n+1}$, and so on . . . .

Thus, the operation of a row addressing device as described with reference to FIGS. 3 and 4 requires the lines to be addressed one after the other, without any pause being able to be made between the addressing of two consecutive rows. Furthermore, the operation of such a device imposes an obligation to address all the rows of a matrix, and does not permit certain lines not to be addressed.

Figure 5:
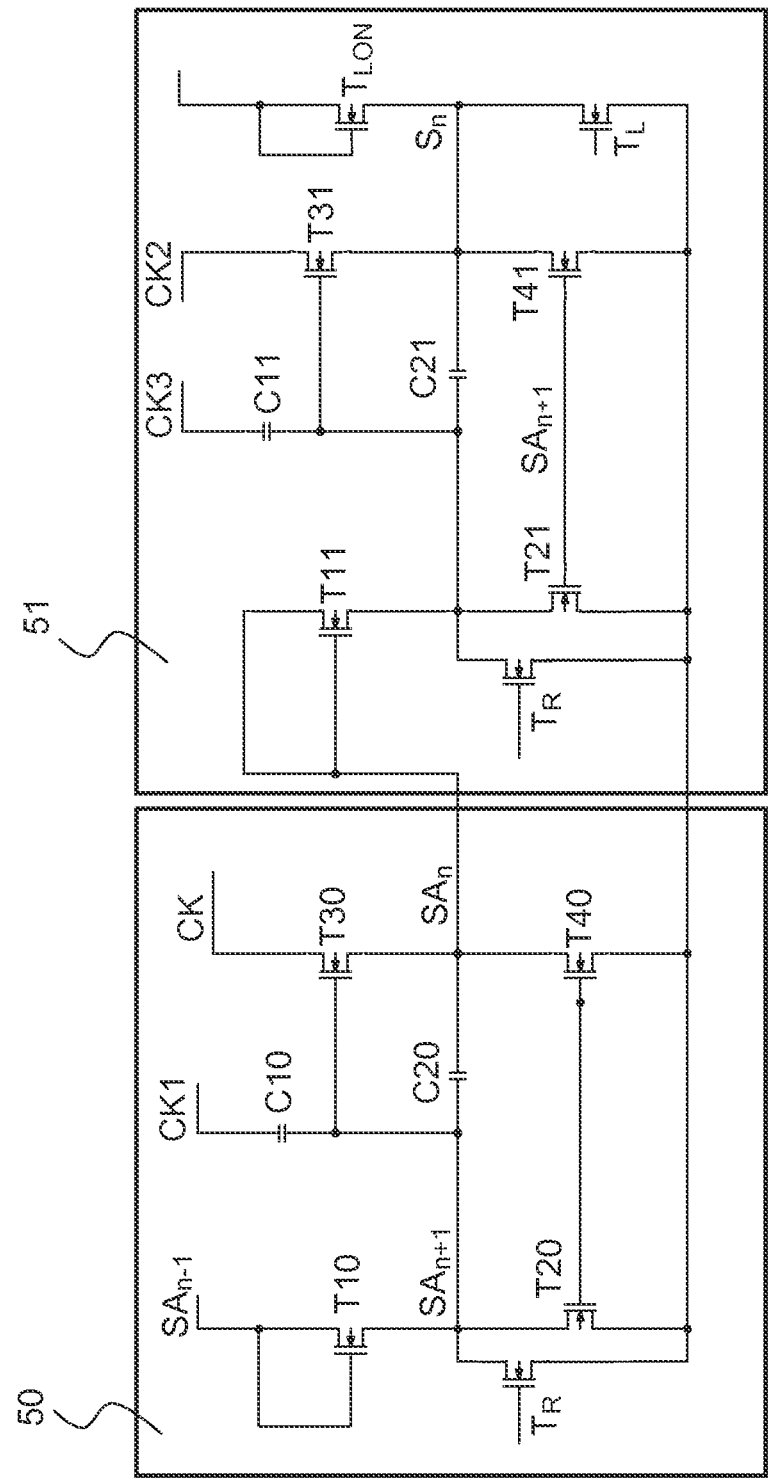
FIG. 5, an electrical circuit diagram illustrating the structure of a stage of a row addressing device, according to an embodiment of the invention.

FIG. 5 shows an electrical circuit diagram illustrating the structure of a row addressing device for a detection matrix, according to an embodiment of the invention.

The present invention proposes that an integrated structure as described previously with reference to FIGS. 1 to 4, illustrating row addressing devices that are applied to a display matrix, be applied to a row addressing device for a detection matrix for ionizing radiation imaging, for example x-ray imaging. The integrated structure forming a row addressing device according to the present invention can essentially comprise TFT transistors of single type, that is to say of P type or else of N type, the N type being able to be preferred for its better performance levels. Thus, all the transistors described hereinbelow can be thin film transistors (TFT) and of single N or P type.

The structure illustrated by FIG. 5 corresponds to an advantageous embodiment in which each stage n of the row addressing device comprises an input stage 50 and an output stage 51. For a stage n of the row addressing device, each of the input and output stages 50, 51 comprises, for example, most of the elements included in a row addressing stage n as described previously with reference to FIG. 3. It should be noted that, in the exemplary embodiments described, each row n of the matrix is associated with a stage n of the addressing device. It is, however, possible, in alternative examples not described by the figures, to envisage structures of row addressing devices in which a given stage controls a plurality of rows, or else in which certain rows are not controlled by a stage.

Thus, the input stage 50 of a stage n of the row addressing device can be formed by a shift register comprising an output line restoring at the output an activation signal SAn. The input stage 50 can comprise an output transistor of the input stage T30, transmitting a pulse of a clock signal at the activation output SAn. The gate of the output transistor of the input stage T30 can be connected to an internal node of the input stage of the addressing device, its source can be linked to the activation output SAn and its drain can receive the signal of a first clock Ck. A step-up capacitor of the input stage C20 can be connected between the gate and the source of the output transistor of the input stage T30. A first control transistor of the input stage T10 is suitable for precharging the gate of the output transistor of the input stage T30. The source of the first control transistor of the input stage T10 is thus connected to the gate of the output transistor of the input stage T30. The gate and the drain of the first control transistor of the input stage T10 are controlled by the activation output SAn−1 of the stage n−1 of the preceding row n−1 addressing device.

A second control transistor of the input stage T20 is suitable for discharging the gate of the output transistor of the input stage T30. The drain of the second control transistor of the input stage T20 is thus connected to the gate of the output transistor of the input stage T30. A compensation capacitor of the input stage C10 can advantageously be arranged between the signal of a second clock Ck1, in phase opposition to the signal of the first clock Ck.

Advantageously, a discharge transistor of the input stage T40 can be connected to the activation output SAn of the input stage 50 of the stage n of the row addressing device. The gate of the discharge transistor of the input stage T40 is linked to the gate of the second control transistor of the input stage T20; it is also linked to the activation output signal SAn+1 of the next stage n+1.

Similarly, the output stage 51 of a stage n of the row addressing device can be formed by a shift register comprising an output line restoring at the output a signal Sn. The output stage 51 can comprise an output transistor of the output stage T31, transmitting a pulse of a clock signal at the output Sn. The gate of the output transistor of the output stage T31 can be connected to an internal node of the output stage of the addressing device, its source can be linked to the output Sn and its drain can receive the signal of a third clock Ck2. A step-up capacitor of the output stage C21 can be connected between the gate and the source of the output transistor of the output stage T31. A first control transistor of the output stage T11 is suitable for precharging the gate of the output transistor of the output stage T31. The source of the first control transistor of the output stage T11 is thus connected to the gate of the output transistor of the output stage T31. The gate and the drain of the first control transistor of the output stage T11 are controlled by the activation output SAn of the input stage 50 of the stage n of the addressing device.

A second control transistor of the output stage T21 is suitable for discharging the gate of the output transistor of the output stage T31. The drain of the second control transistor of the output stage T21 is thus connected to the gate of the output transistor of the output stage T31. A compensation capacitor of the output stage C11 can advantageously be arranged between the signal of a fourth clock Ck3, in phase opposition to the signal of the third clock Ck2. A particular feature of the third and fourth clocks Ck2, Ck3 is that their duty cycles can be different, and that the sum of their respective periods at their high level corresponds to the period of the first and second clocks Ck, Ck1.

Advantageously, a discharge transistor of the output stage T41 can be connected to the output Sn of the output stage 51 of the stage n of the row addressing device, delivering the activation signal of the row n. The gate of the discharge transistor of the output stage T41 is linked to the gate of the second control transistor of the output stage T21; it is also linked to the activation output SAn+1 of the next stage n+1.

According to another specific feature of the present invention, the input stage 50 also comprises a reset transistor of the input stage TR, the gate of which is controlled by a pulse of a reset signal. The source of the reset transistor of the input stage TR can be connected to the sources of the second control transistor of the input stage T20. The drain of the reset transistor of the input stage TR can be connected to the drain of the second control transistor of the input stage T20.

Similarly, the output stage 51 also comprises a reset transistor of the output stage TR, the gate of which is, like the gate of the reset transistor of the input stage, controlled by a pulse of the reset signal. The source of the reset transistor of the output stage TR can be connected to the sources respectively of the second control transistor of the output stage T21 and of the discharge transistor of the output stage T41, and to the sources respectively of the second control transistor of the input stage T20 and of the discharge transistor of the input stage T40. The drain of the reset transistor of the output stage TR can be connected to the drain of the second control transistor of the output stage T21.

Thus, a reset pulse makes it possible to impose, on the different transistors included in the input 50 and output 51 stages, their blocked state.

Furthermore, the output stage 51 can comprise a row reset transistor TL. The row reset transistor TL is controlled via its gate by a specific signal. The drain of the row reset transistor TL is connected to the source of the output transistor of the output stage T31. The source of the row reset transistor TL can be connected to the sources of the transistors T20, T40, T21 and T41. The row reset transistor TL of a stage n makes it possible to force the voltage on the row n to the low state. The row reset transistor TL makes it possible to control the voltage on the rows, that is to say at the outputs of the output stages of the stages, and to apply thereto a low impedance voltage, notably during the "dead times". In practice, typically, the driving of the x-ray detectors, for example, comprises a reset phase, followed by a phase of application of the x rays, or "X window", then a reading phase. During the X window, the x rays are converted into electrons in the photodiodes; the duration of the X window is relatively long, typically up to 3.2 seconds, so the row reset transistor TL makes it possible to avoid any drift of the matrix.

Also advantageously, each output stage 51 can comprise a matrix reset switch, for example formed by a matrix reset transistor $TL_{ON}$ making it possible to produce a complete reset of the matrix. The matrix reset transistor $TL_{ON}$ can be controlled by a matrix reset signal applied to its gate and to its drain. The source of the matrix reset transistor $TL_{ON}$ can be connected to the source of the output transistor of the output stage T31. The matrix reset signal controlling the matrix reset transistor $TL_{ON}$ can be the voltage VGoff or the activation voltage VGon. When the matrix reset transistor $TL_{ON}$ is active, that is to say when the activation voltage VGon is applied, the activation voltage is then applied to all of the matrix.

In practice, a complete reset of the matrix can be produced according to the sequence defined by an activation of the matrix reset transistors $TL_{ON}$ for a sufficient duration, followed by an activation of the row reset transistors TL making it possible to return the rows to the voltage VGoff.

One advantage obtained by the row addressing device as described above with reference to FIG. 5, is that it makes it possible to address the rows in two stages, by offering the opportunity for a pause between the addressing of two consecutive rows. This advantage is a major advantage, notably when the row addressing device is inserted into a system where it is necessary to integrate charges originating from the pixels of the matrix, for example when the latter is used as a sensor, for example for imaging applications such as medical imaging applications. The sensitivity of the plate is, in such a case, all the better as the charge integration time increases. Furthermore, the pause between the addressing of two consecutive rows allows for a driving that is more robust to any matrix defects.

Another advantage obtained by the row addressing device lies in the possibility of making it possible not to address chosen rows as required. This advantage can make it possible to increase the overall speed of the system in which the row addressing device is incorporated, by making it possible not to address certain rows. The input stage 50 can, for example, be addressed very rapidly, by increasing the frequency of the signals of the first and second clocks Ck, Ck1 up to the required row, to reactivate the signals of the third and fourth clocks Ck2, Ck3 when said required row is reached. Such a mode of operation can prove particularly advantageous for applications in which a user, for example in the abovementioned context of the production of imaging by x rays, wants to produce a "zoom" on a particular area of a scene.

Another advantage obtained by the row addressing device lies in the possibility of producing a simultaneous reset of a plurality of rows of the matrix divided up into groups, all of the rows of the matrix being reset by successive resets of the different groups of rows. Such an embodiment can prove particularly advantageous in applications where the matrix is formed by a plate used as sensor, for example for x-ray imaging, and makes it possible notably to reduce the charges induced on the column conductors of the matrix. Such an embodiment is notably described in the patent application FR 2,861,242.

Another advantage obtained by a row addressing device comprising an input stage and an output stage for each row, is that said device is particularly suited to driving matrices of large sizes. In practice, the number of stages per row is still limited to two, and the electrical circuit diagram of a given stage is independent of the size of the matrix. This feature is notably particularly advantageous in medical imaging applications, for which the number of rows can be of the order of several thousand. Typically, the number of rows can be 3000 for sizes compatible with current requirements.

Figure 6:
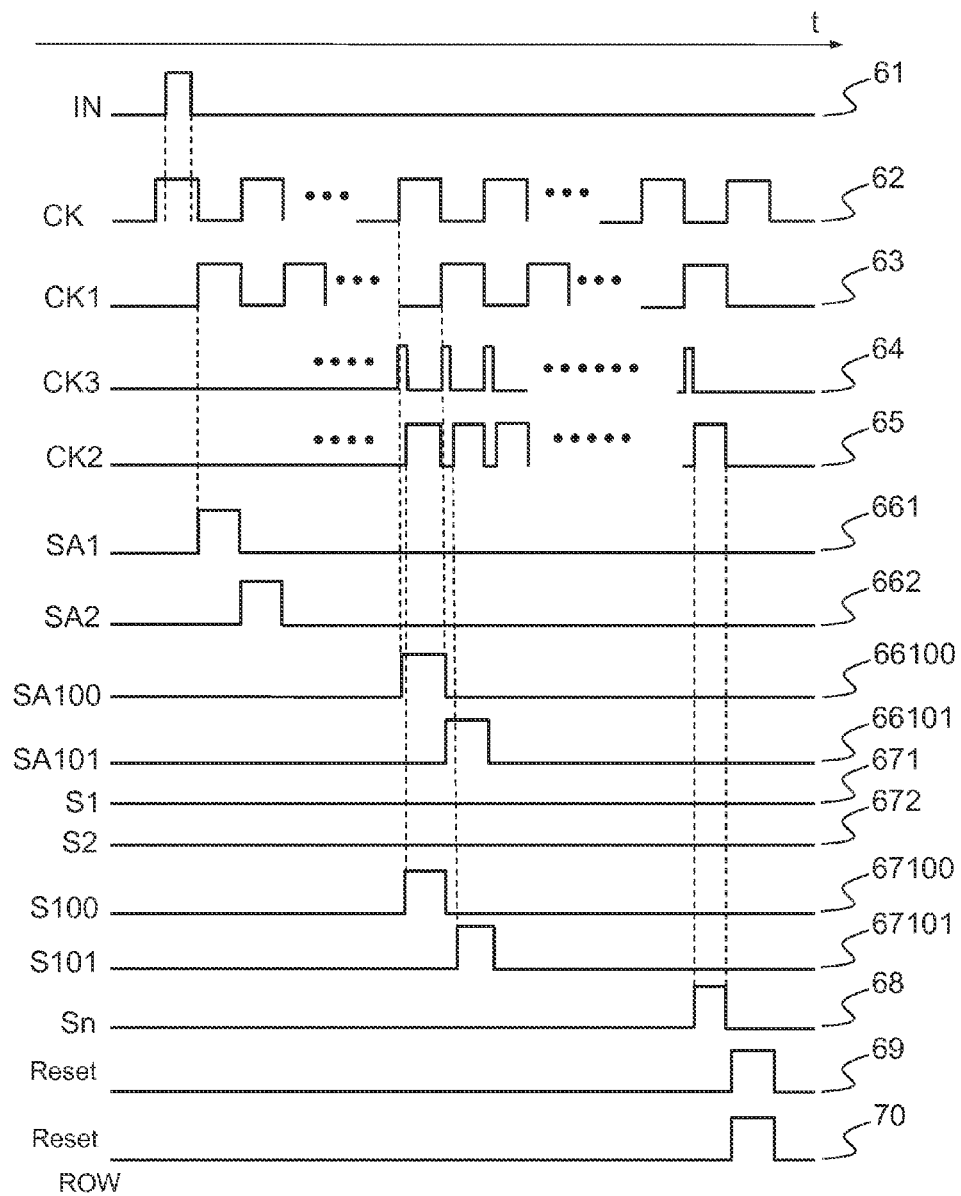
FIG. 6, a timing diagram illustrating the operation of a row addressing device, according to an embodiment of the invention.

FIG. 6 shows a timing diagram illustrating the operation of a row addressing device, according to an embodiment of the invention.

A first timing diagram 61 represents the row scanning triggering signal IN, during a time period corresponding to the transmission of a frame.

A second timing diagram 62 represents, for the same time period, the signal of the first clock Ck; a third timing diagram 63 represents the signal of the second clock Ck1; a fourth timing diagram 64 represents the signal of the fourth clock Ck3; a fifth timing diagram 65 represents the signal of the third clock Ck2.

Four timing diagrams of the activation outputs 661, 662, 66100, 66101 represent, for the same time period, the signals on the activation outputs SA1, SA2, SA100 and SA101 of the input stages corresponding respectively to the rows 1, 2, 100 and 101.

Four timing diagrams of the outputs of the output stages 671, 672, 67100, 67101 represent, for the same time period, the signals on the outputs S1, S2, S100 and S101 of the output stages corresponding respectively to the rows 1, 2, 100 and 101.

An eleventh timing diagram 68 represents the signal of the output SN of the last output stage N of the row addressing device.

A twelfth timing diagram 69 represents the reset signal TR of the input and output stages.

A thirteenth timing diagram 70 represents the row reset signal TL.

When the rows have to be addressed, as is the case in the example illustrated by FIG. 6, for the rows 100, 101 and N, the latter are addressed via the outputs Sn of the corresponding output stages of the row addressing device.

In the example illustrated by FIG. 6, the row scanning triggering signal IN triggers the first and second clocks Ck and Ck1. These clocks provoke, alternately, as is explained previously, the transition to the high state of the activation signals SAn at the output of the input stages n of the addressing device. In the example illustrated by FIG. 6, the activation outputs SAn corresponding to all the rows 1 to N are thus activated. This way, "options", sometimes called "tokens", are taken for the addressing of the rows 1 to N.

The actual addressing of the selected rows is then performed via the third and fourth clocks Ck2, Ck3 allowing for the transition to the high state of the outputs Sn of the output stages of the row addressing device corresponding to the chosen rows. In the example illustrated by FIG. 6, in which the chosen rows are the rows 100 et seq., the third and fourth clocks Ck2, Ck3 are triggered only from an instant corresponding to the row 100, that is to say after 100 pulses of the first clock Ck or of the second clock Ck1. In the example illustrated by FIG. 6, a rising edge of the fourth clock Ck3 coincides with the rising edge of the activation output SA100, then the falling edge of the fourth clock Ck3 coincides with the rising edge of the third clock Ck2, then the falling edge of the third clock Ck2 coincides with the falling edge of the activation output SA100, etc.

Another advantage obtained by the row addressing device comprising an input stage and an output stage for each row, is that the latter is intrinsically protected against interference phenomena linked to capacitive couplings. A row exhibits an equivalent capacitance, the value of which depends on the number of pixels that it contains. This row will then, during reads of the subsequent rows n+1, n+2, etc., be disturbed by capacitive couplings, because the clocks continue to be applied to all the stages, and these disturbances in volts depend directly on the equivalent capacitance of the row. By construction, the row addressing device according to the present invention imposes a voltage corresponding to the low level on a row n for a duration controlled by the clocks, and then leaves this same row n at high impedance. Thus, the more capacitive the rows are, the more stable is the voltage corresponding to the low level on these rows. Furthermore, the disturbances on the voltage corresponding to the low level are linked to the couplings between the clocks and the rows. When a single stage is present for each row, the couplings are significant, because of a parity due to the inversion between the first and second clocks Ck and Ck1 from one stage to another. The fact of adding an output stage not exhibiting any inversion between the third and fourth clocks Ck2, Ck3 means that the couplings between the clocks and the rows are no longer affected by this parity, and the rows are thus disturbed uniformly. Thus, when the matrix is a detection matrix, for which there is typically a reading of the signal present on the columns, the disturbance of the rows is also found on the columns and therefore is added to the signal read. The uniformity of the disturbances due to the use of an input stage and an output stage for each row makes it possible to obtain an image of better quality, unaffected by spatial visibilities as could be the case by using a single stage for each row.

The invention claimed is:

1. A device for addressing the rows of a detection matrix for imaging by ionizing radiations, the detection matrix comprising a plurality N of rows n of pixels and being produced on a substrate, the addressing device also being produced on said substrate mainly from thin film transistors TFT of single N or P type, and comprising a plurality of stages n suitable for delivering at their respective outputs switching signals for switching the high and low levels of a signal applied to switching devices at the output on a corresponding row of the matrix wherein each row n of the matrix is associated with a stage n and wherein each stage comprises an input stage and an output stage, the input stage delivering an activation signal for the output stage, the output stage delivering, in case of activation, said switching signal for the corresponding row n.

2. The row addressing device as claimed in claim 1, wherein each input stage of a row n comprises an output restoring the activation signal, an output transistor of the input stage, transmitting a pulse of a clock signal at the activation output, its gate being connected to an internal node of the input stage, its source being linked to the activation output row and its drain receiving the signal of a first clock (Ck), a first control transistor of the input stage being suitable for precharging the gate of the output transistor of the input stage, its source being connected to the gate of the output transistor of the input stage, its gate and its drain being linked to the activation output of the stage of the preceding row n−1, a second control transistor of the input stage being suitable for discharging the gate of the output transistor of the input stage, its drain being connected to the gate of the output transistor of the input stage.

3. The row addressing device as claimed in claim 1, wherein each output stage of a row n comprises an output restoring the switching signal of the row n, an output transistor of the output stage, transmitting a pulse of a clock signal at the output, of which the gate is connected to an internal node of the output stage, the source is linked to the output of the output stage and the drain receives the signal of a third clock, a first control transistor of the output stage being suitable for precharging the gate of the output transistor of the output stage, its source being connected to the gate of the output transistor of the output stage, its gate and its drain being linked to the activation output of the input stage, a second control transistor of the output stage being suitable for discharging the gate of the output transistor of the output stage, its drain being connected to the gate of the output transistor of the output stage.

4. The row addressing device as claimed in claim 3, wherein a compensation capacitor of the input stage is arranged between the signal of a second clock, in phase opposition to the signal of said first clock.

5. The row addressing device as claimed in claim 3, wherein a step-up capacitor of the input stage is connected between the gate and the source of the output transistor of the input stage.

6. The row addressing device as claimed in claim 3, wherein a discharge transistor of the input stage is connected to the activation output at the output of the input stage, its gate being linked to the gate of the second control transistor of the input stage and to the activation output signal of the next stage n+1.

7. The row addressing device as claimed in claim 3, wherein a compensation capacitor of the output stage is arranged between the signal of a fourth clock, in phase opposition to the signal of said third clock.

8. The row addressing device as claimed in claim 3, wherein a step-up capacitor of the output stage is connected between the gate and the source of the output transistor of the output stage.

9. The row addressing device as claimed in claim 3, wherein a discharge transistor of the output stage is connected to the output of the output stage, its gate being linked to the gate of the second control transistor of the output stage and to the activation output signal of the next stage n−1.

10. The row addressing device as claimed in claim 3, wherein each output stage (51) of a row n comprises a row reset switch configured to impose a low level on the switching signals.

11. The row addressing device as claimed in claim 10, in which the row reset switch is formed by a row reset transistor controlled via its gate by a row reset signal, its drain being connected to the source of the output transistor of the output stage, its source being connected to the sources of the second control transistor of the input stage, of the discharge transistor of the input stage, of the second control transistor of the output stage and of the discharge transistor of the output stage.

12. The row addressing device as claimed in claim 3, wherein each output stage of a row n comprises a matrix reset switch configured to impose a high or low level on the detection matrix.

13. The row addressing device as claimed in claim 12, in which the matrix reset switch is formed by a matrix reset transistor controlled via its gate and its drain by a matrix reset signal, its source being connected to the source of the output transistor of the output stage.

14. The row addressing device as claimed in claim 1, wherein each input and output stage of a row n comprises a reset switch configured to set all the transistors to their blocked state.

15. The row addressing device as claimed in claim 14, in which the reset switches are formed by reset transistors, a reset transistor of the input stage having a gate controlled by a pulse of a reset signal, its source being connected to the sources of the second control transistor of the input stage, and its drain being connected to the drain of the second control transistor of the input stage.

16. The row addressing device as claimed in claim 14, in which the reset switches are formed by reset transistors, a reset transistor of the output stage having a gate controlled by a pulse of a reset signal, its source being connected to the sources of the second control transistor of the output stage, and its drain being connected to the drain of the second control transistor of the output stage.

* * * * *

UNITED STATES PATENT AND TRADEMARK OFFICE
CERTIFICATE OF CORRECTION

| | |
|---|---|
| PATENT NO. | : 9,018,590 B2 |
| APPLICATION NO. | : 14/117010 |
| DATED | : April 28, 2015 |
| INVENTOR(S) | : David Blanchon et al. |

Page 1 of 1

It is certified that error appears in the above-identified patent and that said Letters Patent is hereby corrected as shown below:

In the claims:

Col. 13, line 9, please replace "n-1" with --n+1--.

Signed and Sealed this
Twenty-fifth Day of August, 2015

Michelle K. Lee
*Director of the United States Patent and Trademark Office*